United States Patent [19]

Czech et al.

[11] Patent Number: 5,135,755
[45] Date of Patent: Aug. 4, 1992

[54] CROSS-LINKED HYDROGELS AND THEIR USE AS WOUND DRESSINGS

[75] Inventors: Zbigniew Czech, Koblenz; Kurt Seeger, Neuwied, both of Fed. Rep. of Germany

[73] Assignee: Lohmann GmbH & Co. KG, Neuwied, Fed. Rep. of Germany

[21] Appl. No.: 475,608

[22] Filed: Feb. 6, 1990

[30] Foreign Application Priority Data

Feb. 8, 1989 [DE] Fed. Rep. of Germany ....... 3903672

[51] Int. Cl.$^5$ ...................... A61K 9/70; A61K 47/10; A61L 15/16; A61F 13/02
[52] U.S. Cl. ..................... 424/445; 424/443; 424/444; 424/485; 424/486; 424/487; 424/488; 514/724; 514/738; 514/739; 514/773; 514/774; 514/777; 514/779; 514/801; 523/105; 523/111
[58] Field of Search ............... 424/443, 444, 445, 485, 424/486, 487, 488; 514/2, 21, 724, 738, 739, 773, 774, 777, 779, 801; 523/105, 111; 536/2, 3

[56] References Cited

U.S. PATENT DOCUMENTS 4,572,832  1/1986  Kigasawa et al. .................. 514/773
4,920,158  4/1990  Murray et al. ........................ 524/22

Primary Examiner—Thurman K. Page
Assistant Examiner—Carlos Azpuru
Attorney, Agent, or Firm—Sprung Horn Kramer & Woods

[57] ABSTRACT

The invention relates to a wound secretion absorbing hydrogel of the following composition:
  a) 20 to 70%-wt of at least one multivalent alcohol
  b) 10 to 35%-wt of at least one natural thickener (biopolymer)
  c) 0.05 to 12%-wt of at least one uncross-linked copolymer of one or more vinylcarboxylic acids and their salts (synthetic polymer)
  d) 0.05 to 10%-wt of a cross-linking agent
  e) 0 to 50%-wt of water or physiological saline as well as to the use of this hydrogel as wound dressing.

6 Claims, No Drawings

CROSS-LINKED HYDROGELS AND THEIR USE AS WOUND DRESSINGS

DESCRIPTION

The present invention relates to cross-linked hydrogels on the basis of multivalent alcohols, biopolymers, and synthetic polymers, and to the use of these hydrogels as medical wound dressings.

In recent years a number of hydrogel/colloid systems have come onto the market as wound dressings, said systems exhibit a high absorption capacity for wound secretions so that they may remain on the wound for several days enabling an unimpaired wound healing under elimination of bacteria.

Examples for such materials of hydrogel nature are described on the basis of the following patents:
CA-A 1 180 622 Gelatin+polyethylene oxide+-polyethylenimine
DE-C 28 49 570 Hydrophilic poly(meth-)acrylic acid derivative in the presence of polysaccharide/-protein
DE-C 30 31 304 Basis: hydrophilic ethylenically unsaturated monomers cross-linked with difunctional compounds
EP-B 0 099 758 Synthetic collagens or alginates and other biopolymers
EP-B 0 262 405 Polysodium acrylate/polyacrylic acid/acryloylamide and other acrylamide derivatives
EP-B 0 272 074 Copolymers of unsaturated, carboxyl groups containing monomers+di- or oligosaccharides
U.S. Pat. No. 3,249,109 Gelatin, water, multivalent alcohols, pektin
U.S. Pat. No. 4,243,656 polyacrylate dispersion+humidity absorber, gelatin, water However, wound dressings manufactured in such a way exhibit a number of disadvantages in practice.

Hydrogels on the basis of biopolymers do not exhibit sufficient mechanical strength after absorption of the wound secretions, since the purely physical crosslinking does not provide sufficient stability in the case of high absorption. They dissolve in the wound secretion at body temperature, and thus cannot completely be removed from the wound. Furthermore, such hydrogels are not transparent so that the visual inspection of the wound is not possible without changing the bandage material.

In the case of hydrogels from synthetic polymers the course of the absorption of wound secretion tends to take place discontinuously. In this case, the absorption capacity is exhausted within a relatively short period of time (approximately 2-3 h).

These statements as well apply to products produced according to DE-C 28 49 570 and U.S. Pat. No. 3,249,109 which have to be regarded as nextcoming prior art.

Thus it is the object of the present invention to produce wound secretion absorbing hydrogels which do no longer exhibit the above mentioned disadvantages.

According to the present invention this object is achieved by cross-linked hydrogels on the basis of a combination of multivalent alcohols, biopolymers, and synthetic polymers, whereby biopolymers and synthetic polymer are cross-linked with one another.

Thus the subject matter of the present invention is a wound secretion absorbing, transparent, foil-like, elastic wound dressing obtainable from multivalent alcohols, biopolymers, and synthetic polymers, and crosslinking of the biopolymers with the synthetic polymers.

The hydrogels according to the present invention are built up of the following components:
a) 20 to 70%-wt of at least one multivalent alcohol
b) 10 to 35%-wt of at least one natural thickener (biopolymer)
c) 0.05 to 12%-wt of at least one uncross-linked copolymer of one or more vinylcarboxylic acids and their salts (synthetic polymer) to 10%-wt of a cross-linking agent
d) 0.05
e) 0 to 50%-wt of water or physiological saline As multivalent alcohol glycerol is preferred which can be used alone or in admixture with further multivalent alcohols.

Other multivalent alcohols are ethylene glycol, diethylene glycol, 1,2-propanediol, 1,3-propanediol, 1,2-butanediol, 1,3-butanediol, 2,3-butanediol, 1,4-butanediol, glycerol monoacetate, or a mixture of these alcohols.

As natural thickener (biopolymer) primarily gelatin alone or in admixture with other biopolymers, preferably alginates, are used. Particularly preferred is a combination of gelatin and sodium alginate in a weight ratio of 5:1 to 30:1.

As further biopolymers which are used alone or in admixture with gelatin, collagens and pectins are to be mentioned.

The uncross-linked copolymer used as synthetic polymyer is built up of at least one vinylcarbo acid and at least one of its alkali- or ammonium salts. As vinylcarboxylic acids acrylic acid, methacrylic acid, and/or $\beta$-acryloyloxypropionic acid are preferred. Other suitable vinylcarboxylic acids are vinylacetic acid, maleic acid, fumaric acid, crotonic acid, aconitic acid, itaconic acid, and mixtures of these acids.

The cross-linking agents used according to the present invention are preferably selected from the group consisting of metal chelates, orthotitanic acid esters, epoxides, aziridines, triazines, or melamine formaldehyde resins. Particularly preferred in this connection are aziridines and the group of the metal chelates, e.g., the acetylacetonates, e.g., the transition metal acetylacetonates, such as titanium- or zirconium acetylacetonate. The cross-linking agent effects the cross-linking of biopolymer with synthetic polymer to networks, preferably three-dimensional ones.

The wound secretion absorbing hydrogel according to the present invention is manufactured in that the components are homogenized, optionally under stirring and heating. In this connection it is suitable to add the cross-linking agent to the already homogeneously mixed mass of the other components. The thus obtained polymer mass is then placed on a metallized (preferably aluminized) carrier foil of suitable plastic material, particularly PETP, and, e.g., heated for 20 minutes to 100° C. As finished product a transparent, elastic foil is obtained.

The hydrogel according to the present invention exhibits a surprisingly high water vapour permeability, as well as elasticity and flexibili with those hydrogels on the basis of synthetic polymers and on the basis of biopolymers. Furthermore, the hydrogel according to the present invention rapidly absorbs wound secretions over a comparatively long period of time and, with respect to its absorption behaviour, is clearly superior over the commercial hydrogel on the basis of synthetic polymers which commercial hydrogel achieves its maximum absorption within a comparatively short period of time. The combination of absorption and high water-vapour permeability of the hydrogels according to the uct as described in example 1. The examined values are given in the table, too.

For comparison purposes, hydrogel films on the basis of biopolymers, and on the basis of a synthetic polymer were used, their properties are given in the following table, too.

| Product name | thickness (mm) | color | transparency | elasticity | flexibility | maximum elongation (%) | tackiness | WVP ($g/m^2$ 24 h) | water absorption (24 h) (%-wt) |
|---|---|---|---|---|---|---|---|---|---|
| Cutinova* | 0.23 | colorless | transparent | no, since reinforced | no | 45 (net tears) | no | 39 | 500 |
| Varihesive** | 1.50 | honey-colored | no | no | no | 60 | very sticky | 2085 | 360 |
| Example 1 | 0.56 | yellowy | transparent | good | very flexible | 83 | good adherence | 3461 | 483 |
| Example 2 | 0.58 | yellowy | transparent | good | very flexible | 105 | good adherence | 2603 | 450 |
| Example 3 | 0.60 | yellowy | transparent | good | very flexible | 210 | good adherence | 2477 | 468 |

*Cutinova: composition: polyvinyl alcohol
**Varihesive: Composition: gelatin, carboxymethyl cellulose, tackifying resins present invention effects a constant humid environment on the wound which leads to an acelerated healing. Furthermore, the hydrogels according to the present invention are transparent and thus make possible observation of the wound healing process so that change of bandage material in the case of wounds with low secretion can be carried out within longer intervals.

Compared with the known hydrogels on the basis of biopolymers, the hydrogels according to the present invention are superior - in addition to transparency, elasticity and flexibility - particularly with respect to the fact that they do not dissolve in the wound secretion.

The invention further relates to the use of the hydrogels according to the present invention as wound dressings.

The following examples illustrate the present invention but are not construed as limiting:

EXAMPLE 1

A mixture of 70 g glycerol, 30 g gelatin, 30 g water, and 5.4 g copolymer of acrylic acid and sodium acrylate (18% solution in glycerol/water 3:1) are homogenized in a 1-1 flask under constant stirring at 95° C. 18 g titanium acetylacetonate in form of a 10% alcoholic solution are added to the molten homogeneous mass.

An aluminized PETP-foil is coated with the so obtained polymer mass and heated for 20 minutes to 100° C. As finished product a transparent, elastic foil is obtained the properties of which are stated in the table.

EXAMPLE 2

30 g aluminum acetylacetonate in form of a 5% ethylacetate solution is mixed to the molten mass described in example 1. The properties of the hydrogel obtained after coating and drying (20 min at 100° C) are shown in the following table.

EXAMPLE 3

Similar to example 1, a mixture of 60 g glycerol, 10 g 1,2-propanediol, 35 g gelatin, 45 g water, and 6.2 g copolymer of β-acryloyloxypropionic acid and potassium-β-acryloyloxypropionate (15% solution in glycerol/water 4:1) are homogenized under constant stirring at 95° C. The molten mass is mixed with 4.5 g melamine formaldehyde resin and processed to the finished product as described in example 1. The examined values are given in the table, too.

The tested hydrogels show a different absorption course, whereby the commercial hydrogel on synthetic polymer basis ("Cutinova") achieves its maximum absorption already after 2 to 3 hours.

Compared with other hydrogels, the hydrogel according to the present invention exhibits an excellent water-vapour permeability (WVP) which in combination with a rapid absorption of wound secretions leads to the fact that always a constant, healing-promoting humid environment on the wound is present, independently from the amount of secretion.

We claim:

1. Cross-linked, wound secretions-absorbing hydrogels, characterized in that they are built up of the following components, the biopolymers and synthetic polymers being inter-crosslinked:
   a) 20 to 70 % by weight of at least one multivalent alcohol selected from the group consisting of glycerol, ethylene glycol, diethylene glycol, 1,2-propanediol, 1,3-propandediol, 1,2,-butanediol, 1,3-butanediol, 2,3-butanediol, 1,4-butanediol and glycerol monoacetate,
   b) 10 to 35% by weight of at least one natural thickener (biopolymer) selected from the group consisting of collagen, gelatin, pectins and a mixture of gelatin/sodium alginate in the ratio of 30:1 to 5:1,
   c) 0.05 to 12% by weight of at least one uncrosslinked copolymer of one or more vinylcarboxylic acids and their salts (synthetic polymer),
   d) 0.05 to 10% by weight of a cross-linking agent, and
   e) 0 to 50% by weight of water or physiological saline.

2. The cross-linked, wound secretions-absorbing hydrogels according to claim 1, characterized in that in copolymer c) the alkali metal salts and/or ammonium salts are used as salts of the vinylcarboxylic.

3. The cross-linked, wound secretions-absorbing hydrogels according to claim 1, characterized in that the ratio poly-vinylcarboxylic acid/ polyvinylcarbonic acid salt in copolymer c) is in the range of 10:1 to 1:10.

4. The cross-linked, wound secretions-absorbing hydrogels according to claim 1, characterized in that the vinylcarboxylic acid of copolymer c) is acrylic acid, methacrylic acid, or β-acryloyloxypropionic acid, vinylacetic acid, maleic acid, fumaric acid, crotonic acid, aconitic acid, and/or itaconic acid.

5. The cross-linked, wound secretions-absorbing hydrogels according to claim 1, characterized in that the cross-linking agent d) is selected from the group consisting of metal chelates, orthotitanic acid esters, epoxides, aziridines, triazines, or melamine formaldehyde resins.

6. The cross-linked, wound secretions-absorbing hydrogels according to claim 1, characterized in that the cross-linking agent d) creates three-dimensional networks of biopolymers and synthetic polymers.

* * * * *

UNITED STATES PATENT AND TRADEMARK OFFICE
CERTIFICATE OF CORRECTION

PATENT NO. : 5,135,755
DATED : August 4, 1992
INVENTOR(S) : Czech et al.

It is certified that error appears in the above-identified patent and that said Letters Patent is hereby corrected as shown below:

Col. 4, line 42  Delete propandediol " and substitute -- propanediol --

Col. 4, line 58  After " vinylcarboxylic " insert -- acid --

Col. 4, line 61  Delete " polyvinylcarbonic " and substitute -- polyvinylcarboxylic --

Signed and Sealed this

Seventh Day of June, 1994

BRUCE LEHMAN

Attest:

Attesting Officer

Commissioner of Patents and Trademarks